United States Patent
Dewan

(10) Patent No.: US 6,681,774 B2
(45) Date of Patent: Jan. 27, 2004

(54) PROCEDURES TO PREVENT ALZHEIMER'S OR ENHANCE RECOVERY FROM BRAIN DAMAGE BY USE OF PROCEDURES THAT ENHANCE REM SLEEP

(75) Inventor: Edmond M. Dewan, Lexington, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 319 days.

(21) Appl. No.: 09/907,877

(22) Filed: Jul. 13, 2001

(65) Prior Publication Data

US 2003/0150465 A1 Aug. 14, 2003

(51) Int. Cl.$^7$ ............................................... A61B 19/00
(52) U.S. Cl. ....................................................... 128/898
(58) Field of Search ........................ 424/247; 128/898; 607/45, 118

(56) References Cited

U.S. PATENT DOCUMENTS 3,879,552 A * 4/1975 Gogerty ....................... 424/247
5,299,569 A * 4/1994 Wernicke ..................... 607/45

* cited by examiner

*Primary Examiner*—Michael A. Brown
(74) *Attorney, Agent, or Firm*—William G. Auton

(57) ABSTRACT

A brain damaged patient who is improving will have a higher percentage of REM sleep than one who is not. The improvement we studied is that occurring over a period of weeks and months, so it cannot be attributed to the return of function of temporarily damaged, but not destroyed, brain tissue. Improvement was therefore to be considered as new learning or programming. Patients suffering from aphasia as the result of a discrete cerebrovascular accident or of trauma are able to enhance their improvement by increasing amounts of REM sleep inducing activities (such as having a regular sleep schedule with a systematic schedule of phase changes in circadian rhythms) and diminishing REM sleep reducers such as caffeine, noise or a use of tranquilizers.

2 Claims, No Drawings

PROCEDURES TO PREVENT ALZHEIMER'S OR ENHANCE RECOVERY FROM BRAIN DAMAGE BY USE OF PROCEDURES THAT ENHANCE REM SLEEP

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to recovery from brain disorders and more specifically to a procedure to enhance REM sleep.

Alzheimer's Disease is a progressive neurodegenerative disorder affecting 7% of the population over 65 years of age and characterized clinically by progressive loss of intellectual function. This impairment of function is caused by the presence of neuritic plaques in the neocortex and the loss of presynaptic markers of cholinergic neurons. Neuritic plaques are composed of degenerative axons and nerve terminals, often surrounding an amyloid core and usually containing reactive glial elements. Another characteristic pathologic feature of Alzheimer's Disease is the neurofibrillary tangle, which is an intraneuronal mass which corresponds to an accumulation of abnormally phosphorylated tau protein polymerized into fibrillar structures termed paired helical filaments. In addition, the neurofibrillary tangle also contains highly phosphorylated neurofilament proteins. Even the earliest papers on Alzheimer's Disease were clear that both "senile" plaques and neurofibrillary tangles had to be present in abundance to allow a post-mortem diagnosis of the disease.

Many treatments for recovery from brain disorders center around the presumption of chemical agents. An example of this approach is described in U.S. Pat. No. 6,228,878, May 8, 2001, Methods for treating or preventing Alzheimer's disease using substituted 2-aryl-3-morpholinopropanones, DeBernardis, John, the disclosure of which is incorporated herein by reference. An alternative to prescriptive chemical agents is using procedures to enhance REM sleep, as described below.

This process is based on observations published by E. M. Dewan in "Nature", Volume 223, No. 5202, pp. 183–184 in 1969 that a brain damaged patient who is improving has a higher amount of REM sleep than one who is not improving as well.

SUMMARY OF THE INVENTION

The present invention is a process to prevent Alzheimer's disease and enhance recovery from brain damage afflictions. This process is made up of steps to maximize REM sleep as discussed below.

DESCRIPTION OF THE DRAWINGS

This patent contains no drawings.

DESCRIPTION OF THE PREFERRED EMBODIMENT

Since the discovery of particular physiological changes associated with dreaming, it has often been suggested that dreaming or rapid eye movement (REM) sleep is a form of information processing. Some of these proposals have used computer analogies, others have been deduced from the kinds of perceptual events that occur in dreams, and some are derived from the nature of the mental changes, which follow dream deprivation. Some of the models suggest that REM sleep serves to discard extraneous information. Another possibility is that any long term functional reorganization in the brain must be done with the help of REM sleep; that is to say, REM sleep is necessary for adding new information to existing stores or structures—in other words, a kind of programming of the brain occurs during REM sleep.

This hypothesis predicts that a brain damaged patient who is improving will have a higher percentage of REM sleep than one who is not. The improvement we studied is that occurring over a period of weeks and months, so it cannot be attributed to the return of function of temporarily damaged, but not destroyed brain tissue. Improvement was therefore to be considered as new learning or programming. Patients suffering from aphasia as the result of a discrete cerebrovascular accident or trauma are suitable for this work. The increase in their speech production or comprehension can be determined quite easily. We assume that in patients who are learning to produce or understand new words, information is being added to the nervous system; this should be reflected by higher levels of REM sleep than in patients who show no improvement.

Eighteen aphasic patients were selected by the staff of the Neurology Service of the Boston V.A. Hospital. The patients varied in their rate of improvement and the severity of the aphasia, but this information was withheld from us until we had completed our studies of their sleep. We studied the patients with all-night electroencephalograph (EEG), electro-oculogram (EOG) and electromyogram (EMG) recording. All but four of the patients were studied at least two nights. The records were scored for REM sleep with the usual criteria of a low voltage mixed frequency EEG with REM and a decrease in muscle tone following a period of slow wave or spindle sleep. The patients were not receiving medication during the study.

TABLE 1

A COMPARISON OF PERCENTAGE REM SLEEP IN IMPROVING AND NON-IMPROVING APHASIC PATIENTS

| Subjects with no improvement | | | Subjects with clear improvement | | |
|---|---|---|---|---|---|
| Subject | Percentage REM Sleep | REM (min) TST (min) | Subject | Percentage REM Sleep | REM (min) TST (min) |
| 1 | 4 | 9/212 | 1 | 23, 27 | 48/211, 114/420 |
| 2 | 12 | 22/181 | 2 | 23, 26 | 106/461, 94/368 |
| 3 | 20.15 | 62/315, 54/373 | 3 | 16, 11 | 66/108, 40/355 |
| 4 | 12.6 | 48/388, 20/305 | 4 | 25, 18 | 90/348, 67/380 |
| 5 | 25.18 | 59/239, 5 49/274 | 19 | | 67/353 |
| 6 | 15 | 64/411 | 6 | 16, 17 | 59/362, 47/271 |
| 7 | 16.7 | 52/327, 22/338 | | | |
| 8 | 13.6 | 47/350, 17/286 | | | |
| 9 | 10.11 | 30/308, 28/252 | | | |
| | | N = 15 nights | | | N = 11 nights |
| Average | 127 | 39/310 | | 201 | 73/538 |

Significance of difference average: t test: t = 3.48–0.005 < P <0.001.
Mann-Whitney: U = 28 0.005 < P < 0.001.

TABLE 2

A COMPARISON OF PERCENTAGE REM SLEEP IN THE MOST SEVERE AND LEAST SEVERE GROUPS (ON A SCALE OF 0–3) (SIZE AND RATE OF IMPROVEMENT ALSO SHOWN FOR COMPARISON)

| | Severe (2+ or 3) | | | | Less severe (0–1 or 2) | | |
|---|---|---|---|---|---|---|---|
| Subject | Percentage REM sleep | Imp. | Size* | Subject | Percentage REM sleep | Imp. | Size |
| 1 | 4 | − | 2 3 | 1 | 16, 11 | + | 1 |
| 2 | 12 | − | 2 | 2 | 25, 18 | + | 1 |
| 3 | 20, 15 | − | 4 | 3 | 19 | + | 1–2 |
| 4 | 12, 6 | − | 2 | 4 | 25, 18 | − | 3–4 |
| 5 | 15 | − | 3 | 5 | 16, 7 | − | 4 |
| 6 | 13, 6 | − | 2 3 | | | | |
| 7 | 10, 11 | − | 3 1 | | | | |
| 8 | 23 | + | 5 | | | | |
| 9 | 16, 17 | + | 2 3 | | | | |
| | N = 11 nights | | | | N = 9 nights | | |
| Average | 129 percent | | | | 172 percent | | |

Mann Whitney U test. U − 31 0.1 > P > 0.05.
*Size estimated by brain scan on scale of 1–5 with 1 the smallest.

The clinical severity of the patients' aphasia and their rate of improvement at the time of the sleep studies were rated by the two speech therapists and the head of the Aphasia Unit. Both severity and improvement were rated on scales of 0–3. On the improvement scale—3 was dramatic, 2 clearly perceptible each week, 1 barely perceptible and 0 was for no detectable improvement. For severity—0 was for barely perceptible aphasia and 3 for total aphasia or almost so. The ratings were based on the patients' clinical progress and performance in regular speech therapy sessions. Data were also available from brain scans about the size of lesion in some patients. When rated by improvement, those with least improvement were compared with those with most improvement. Three patients with slight improvement, where there was no clear agreement among the neurology staff, were eliminated. When the percentage of REM sleep of these groups was compared there was a significant difference. Table 1 shows that non-improving patients averaged 12.7 percent REM sleep while improving patients showed 20.1 percent. The differences were significant at the 0.005 level with both the t test and the Mann-Whitney U statistic. While three of the four patients who had only one night in the laboratory were in the non-improving group, it is interesting to note that the non-improving group showed a lower percentage of REM sleep the second night than the first, so that the single nights could not have artificially lowered this group's results because of a "first night" effect. When the effect of severity on levels of REM sleep were examined, a similar difference (0.1>1'>0.05), although not as striking, was noted (Table 2). The most severely aphasic patients had lower levels of REM sleep than the less severe patients did (12.9 percent and 17.2 percent respectively). There was considerable positive correlation between severity and lack of improvement. Two patients who were rated as most severe did, nonetheless, show significant improvement and their levels of REM sleep averaged about 20 percent, and two patients who were in the least severe group showed no improvement with an average of 16 percent REM sleep. Furthermore, the patient with the largest lesion measured by brain scan showed improvement. Thus there was not a complete correlation between severity and improvement, and improvement appeared to be the chief factor in the level of REM sleep.

Our results are consistent with the hypothesis that recovery of function after brain damage involves a process of programming associated with REM sleep. The fact that severity of disability was not closely associated with a change in the percentage of REM sleep, and that lesions were in different parts of the cortex, makes it less likely that the size or location of the lesions produced the lower percentages of REM sleep in the non-improving patients. Feinberg, in his studies of patients with chronic brain syndrome, also found decreased levels of REM sleep. His diagnosis indicates that this was a group with brain damage of varying severity, but with no improvement occurring at the time of study. On the other hand, Feinberg found with mentally retarded children that the lower the I.Q., the lower the amount of REM sleep. It seems probable that there is a correlation between I.Q. and amount of new information being added to the nervous system.

We realize that to establish REM sleep as necessary for the improvement we need to perform dream deprivation studies with brain-damaged patients. But our present findings are evidence of a relationship between a clearly existing reprogramming situation (improvement in aphasia) and higher levels of REM sleep.

THE PROGRAMMING (P) HYPOTHESIS FOR REM SLEEP

The Use of Theory in Sleep Research

At the present stage of development of sleep and REM research, enough facts have accumulated to make it inconvenient for anyone to memorize them all. Whenever this happens in a particular discipline, conceptual schemes are usually developed which, at least in a limited was, make "sense" out of these facts by providing a background or context in which these facts fit together coherently. When such schemes are successful, one can deduce the facts from a small number of basic hypotheses and can thus "remember" what is known. These conceptual schemes, of course, are called models or theories and, if they are to be taken really seriously, they must also give rise to new experimental predictions. Inevitably, theories must be modified in the light of new experiments, but their helpfulness consists not in their "correctness" but in their ability to direct experimental investigation. Theory can thus be regarded as a convenient tool to help recall facts and also to guide experiments.

In this patent, a hypothesis is advanced which has already shown itself useful in these respects. In the attempt to learn its limitations we have learned some startling facts. It is almost certain at the outset that this hypothesis has limitations and must be modified accordingly, but this is totally irrelevant. The strength of the hypothesis is entirely in its "vulnerability" to test and to the large number of tests it suggests. Space limitations allow the discussion of only a few of the total number of possible experimental predictions and questions, but these will suffice to illustrate the technique.

The Heuristic Development of the P (Programming) Hypothesis: We begin by pointing out some general observations which lad to the suggestion that REM sleep is related to a process of functional structures (programs) in the brain.

First, there is the observation that biological phenomena ranging from adaptation, evolution, and homeostasis to learning behavior all exhibit the "error correction" or "optimization" effects so common in any control system. In other words, the concept of feedback in its various forms is one of the most intrinsic phenomena to living processes. This sort of observation is especially pertinent to the ability of higher animals to learn and adapt to changing situations throughout their lifetimes. The further, reasonable postulate that nature is "economical' or nearly "optimal" implies that brains of such animals would be set up to perform functions relevant to the current needs of the animal. The information which is no longer needed by it would presumably be stored more economically at the price of accessibility, and so on. In short, we hypothesize that the brains of higher animals are in a state of constant alteration in the sense that their functional structure is constantly being revised for current situations or needs. This is analogous to programming and reprogramming in the computer. In my opinion there is no question that it takes place. The question is only of when and how it happens. One's first guess might be that sleep plays an important role since the animal disconnects in some sense from the environment in that condition, and this would be necessary if reprogramming must be done "off line," as they say in the computer business.

Two of the most indicative observations about REM sleep (D-state) are (1) the phylogenetic development which increases from zero percent in the lowest and least adaptable (fixed programmed) animals to about 25 percent of sleep on the average for the mammals, and (2) the ontogenetic development which decreases from birth and childhood (when the animal is most plastic and able to learn) to adulthood and senility when learning and memory recall for new memories are at their lower values. In this connection it has been estimated that at about 24 to 30 weeks gestational age in the human fetus, 100 percent of sleep is in REM sleep. This is especially interesting from our point of view since presumably the initial programming of the brain occurs at a maximum rate during earlier stages of the embryo's development.

The most theoretically compelling of early observations about REM sleep, in the context of the above remarks, are these: (1) REM sleep is associated with dreams, and (2) percent of REM sleep rebounds after suppression, implying it does something of importance to or for the organism.

Thus we are led to make a guess or hypothesis that REM sleep plays an important role in programming the brain. But this general statement lacks the precision or vulnerability necessary to suggest experiments to directly test (i.e. disprove) it. In the following, therefore, we prefer to consider what limitations and qualifications must be made to the statement that "REM sleep is necessary and sufficient for P." In this way we hope eventually to arrive at the simplest theory possible—but we must of necessity begin with one simpler than possible.

The organization of the remainder of this paper is as follows: (1) the examination of six aspects of P (programming), (2) the discussion of some known facts in this context, and (3) the deduction of experimental predictions and important experimental questions from the hypothesis.

THE CONCEPT OF P IN THE COMPUTER AND THE BRAIN

In modern computers there are two methods employed to set up programs or functional structures. The first is to connect various computing components with an arrangement of wires, which can be plugged or unplugged from a "patch panel." The other is to store instructions in the form of coded numbers in the computer memory ("memory stored control"). During computer operation these instructions are called forth in sequence. Changing the program consists of replacing instructions in the memory device. In either type of programming one has an alterable functional structure, and we are hypothesizing that in the brain the functional structures ("pathways") can also be altered. Some computers can automatically reprogram themselves in some sense; however, a human programmer is responsible for most of the significant changes and the creation of new programs. In this paper we hypothesize that the brain has a method of reprogramming itself spontaneously and automatically.

The six categories of P to be considered (involving experiments from several disciplines) are these: (1) physical or structural aspects, (2) memory aspects, (3) input-output (I-O) programs having to do with perception, sensory motor coordination, motor skills, and attention phenomena, (4) organization of P by emotion and drive, (5) homeostatic and biorhythmic aspects of P, and (6) P-system breakdown.

DETAILED DESCRIPTIONS, EXPERIMENTAL PREDICTIONS, QUESTIONS, AND RESULTS

Physical aspects of P: The P needed for the following tasks is included in this category: (1) establishing new functional pathways as neurons die with age and are not replaced (at the rate of 1000 to 10,000 per day), (2) initial programming of the embryo brain, and (30 establishing new functional pathways after brain damage. This aspect of P is in some ways analogous to wound healing, metamorphosis, morphogenesis, and regeneration, in that macroscopic structures are organized in an adaptive manner. There is an especially great similarity between the brain and a developing embryo since in both cases (presumably) macromolecules in some way control the development of global structures, and vice versa. For this reason a better understanding of morphogenesis may have relevance to neurophysiology in connection with the P process.

These notions raise interesting questions: 1. Does long-term deprivation of REM sleep cause permanent physical damage? (We'd expect the answer to be yes because of the neuron deaths) 2. Does REM deprivation in the embryo (e.g. by drugs) cause it to be malformed or inhibit the natural anatomical growth of the brain? (Prediction: yes) Do embryos of even the lower forms show high amounts of REM sleep at some early stage? (Prediction: yes) Adametz's observation that a lesion which is made in two steps is dramatically less damaging functionally than if made all at once is quite suggestive of P processes. A prediction is that if REM deprivation is carried out during the interval of time between making the lesions there would be almost as much damage as when the lesions were made all at once. If this is true, it would be an impressive confirmation of the model.

Another approach to testing this phenomenon is to measure percent of REM sleep in aphasics who are rapidly improving and compare this to percent of REM sleep in those who are not improving. It has been shown that there is a (statistically significant) higher amount of REM sleep in the subjects who are improving, as the hypothesis predicts. The next experiment would be to see if REM deprivation temporarily cuts down improvement in those subjects.

Memory P: In a computer, the use of memory devices is organized according to a hierarchical principle: the less frequently used material is stored in progressively slower but more economical memories. Memories can be shifted to different devices as priorities change. There is an analogy to the brain's memory in that as information is used less often it can become no longer recallable but still recognizable— and so on until the memory manifests itself only in a savings in relearning time. In both cases the accessibility of information is optimized with respect to the memory structures available and to priority.

One special form of early learning, imprinting, also falls into the category of the memory type of P and we would expect high amounts of REM sleep during critical periods.

We shall assume in the following that REM sleep has to do with the consolidation of memory into the best configuration for the organism's needs (cf. later section on Organization of P by Drives and Goals).

According to the P hypothesis one can deduce the following predictions: (1) the Korsakoff patients who show practically no ability to recall should have no REM sleep. (2) Electroconvulsive therapy (ECT) which causes amnesia should decrease REM pressure. (3) lower animals (e.g. birds) when being subjected to a regimen of high amounts of learning (e.g. during operant conditioning experiments) would show more REM sleep. The first prediction was tested and it was found that there was REM sleep in Korsakoff patients but that it was physiologically abnormal, suggesting that "abnormal REM" can occur without evidence of p. The prediction about ECT is true in the sense that REM deprivation will not give an REM rebound on a successive night if ECT intervenes. The third prediction is as yet unexplored.

Many other investigators have examined the memory aspect of "P". Greenberg, Pearlman, Fishbein, Feldman and others have obtained evidence that REM sleep plays a role in memory processes. Briefly, their work suggests that REM sleep may involve both a necessary preparation for learning (a form of "metaprogramming") and also a form of consolidation of information (for long term memory). In addition it has been substantiated that chicks have large amounts of REM sleep shortly after hatching, i.e. during the critical imprinting time. Further work with REM suppressing drugs (predicted to block imprinting) remains to be done, and it would also be of interest to see if nitrous oxide can cause imprinting to occur (on the basis that nitrous oxide can bring on a state similar to REM sleep). Another important imprinting experiment would be to see if there is an REM sleep increase in ungulates during adult imprinting. If this came out positively it would suggest that some animals (i.e. those that exhibit "imprinting" in a dramatic way) are "reflex programmers" and therefore show a low percent of REM sleep most of the time, and others are "spontaneous programmers"—i.e. have REM sleep even when not crucially needed. It would further substantiate the connection between REM sleep and P, since observations to date on REM sleep in chicks may also be explained merely by the ontological development, and not necessarily by the P hypothesis.

Input-output (I-O) P Perhaps the least explored area of research on REM sleep concerns the I-O programs of the brain. These consist of the programs having to do with the organization of perception, coordination of motor activity (acquisition of motor skills), coordination of sensori-motor relations, coordination of motor activity directly controlling perception (especially eye motion in visual perception), and finally attention programs which automatically filter the sense modalities and present the brain with the most relevant incoming information. These programs are assumed to be optimized in some sense to the organism's current needs (cf. The next section).

The first and only experiment to date that has been performed involved the adaptation to visual field rotation (180°). Originally Kohler and Held noted that subjects Could adapt to visual rotation and distortion provided they exercised willed motor activity over a certain interval of time. This of course is P, therefore the prediction is that visual field inversion, and so on, should enhance REM sleep time and REM intensity (provided there was willed motor activity 0. Both were in fact observed. This result, if substantiated by more extensive controlled tests, opens up an entirely new area for REM experimentation. Consider the new question raised: "Does ECT hamper adaptation to visual distortion in view of the fact that it decreases REM pressure? Do REM suppressing drugs delay adaptation? Can Korsakoff patients with their "abnormal REM" adapt? Do children (with higher REM sleep time) adapt faster than adults? Can lower forms ever adapt (with no REM sleep)? What happens if imprinting animals have their visual fields inverted during the critical period? What happens to REM sleep in schizophrenics if they have visual inversions? Is there an absence of the increased REM effect if the subject has visual inversion but performs no "willed motor activity" of consequence? This list can easily be extended to the reader, and the predictions of the model are obvious.

Numerous other forms of sensorimotor experiments suggest themselves involving percent of REM sleep and REM deprivation effects relative to learning to cope with conditions of weightlessness, sensorimotor time delay (using video tape recording for the visual delay), "human amplification situations"—e.g. having a man learn how to operate a vehicle or "construction equipment," and so on—all of which involve the development and incorporation of sensorimotor programs. In all of the above, dream content should be examined for relevance. One should also investigate REM effects and dream content in athletes preparing for a contest.

The attention P aspects of REM sleep might be examined, for example, by measuring contingent negative variation (CNV) patterns in a student pilot training in a cockpit simulator: REM sleep should be more intense during a concentrated training regimen, REM deprivation should cut down learning, and the CNV patterns, which theoretically should reflect the patterns of anticipated events for attention, would not become efficient as quickly, and so on.

Organization of P by Drives and Goals: It will be assumed that the intensity of an emotion is directly related to ability or inability to "cope," i.e. to the need for P. According to Simontov, a surplus amount of "ability to cope" gives rise to a pleasurable emotion and vice versa. It is also related to the strength of the associated drive. Thus, taking these two facts together it is an ideal measure for the priority of areas that need P. Assuming this, the amount of emotionality experienced by a subject should affect REM pressure. An increase in emotion should lead to an increase in amount or intensity of REM sleep and vice versa. This might explain why some tranquilizers which decrease emotionality also reduce REM pressure. From this one would also expect REM deprivation to increase emotionality, given that the subject needed to cope with a new situation for which he was not prepared. These considerations also have obvious implications for dream content. Some experiments with stressful moving pictures support this prediction.

We shall assume that emotion plays an additional role in programming, namely that it is used for tagging or labeling memories and programs for the purpose of consolidation during the P process. This could only be possible if the variety of emotional nuances or feelings were as great as the variety found in perception. This will be assumed here in spite of the lack of variety of verbal representation for these feelings. As Plutchik has shown, there is evidence that emotional feelings are internally perceived and processed in a manner abstractly resembling color perception. Associated with each goal or drive would be a certain set of feelings which would then tag the perceptions and experiences occurring at any given time. We then hypothesize that during the P process all memories, programs, and so forth which are relevant to a current important need can be brought together and "filed" in one place by making use of these tags. This is analogous to the computer technique known as "associative memory" in which the address number of each memory location includes a coded numerical tag to identify the type of information stored there.

This scheme is suggested partly by Freud's description of dream content: displacement, condensation and symbolism, "primary process logic," and the organization of materials by drive, wish and instinctive needs. It can be shown that these aspects of dream content resemble a clever way to scan experience and organize information according to needs by the use of "feeling nuances" as tags. This will be described in detail elsewhere; however, a great deal of independent work, which should be consulted, has also been done by Breger along similar lines.

The phenomenon of state dependent memory is entirely consistent with this viewpoint. The "state" can be regarded as a constellation of feelings. The model suggests that the available P's of all the types—I.O., perceptual, and behavioral, as well as memory—should be state dependent. For example, the question is now raised: "Can adaptation to distorted vision be state dependent?" In addition, this hypothetical mode of operation of the P system suggests certain causes of breakdown (discussed in the later section on that subject).

REM Periods, Homeostasis, and Biological Rhythms: Sleep and REM periods are both "gated" by biological rhythms (of approximate periods of 24 hours and 90 minutes, respectively). In this model, P (in all its aspects) is regarded as a form of complicated homeostasis which involves not only the animal's "ability to cope" but its mental processes and the entire range of physical bodily processes in support of this. Since REM sleep is locked in step to the bodily rhythms, it is tempting to conjecture that the hypothetical P processes they represent can in turn affect these rhythms. For example, the observations of Stroebel suggest that the body can be programmed for a certain type of emotionality as a function of time of day. More specifically, if an animal is repeatedly stressed at one time of day for several days, this tendency for stress will continue to appear at the time with circadian regularity and will not easily be extinguished unless it is deconditioned at that time of day (the time of day thus representing a "state" in a state dependent learning response). This suggests that P can program the hormone releases, and other somatic and homeostatic anticipatory activity to prepare the animal to "cope". REM deprivation should tend to prevent this; hence, an important experiment would be to repeat Stroebel's work but with REM deprivation. Other questions raised are these: (1) Does a large phase change of the circadian rhythms increase REM sleep? (Prediction: Possibly yes). (2) Can the length of the circadian rhythm (free running) depend on "need for P"—i.e., increase in length due to a greater need for P? In other words do emotionally disturbed people or people with a large need for P for one good reason or other need more sleep and tend to wake up later in the morning and go to bed late? Theoretically there would be a delayed phase due to a longer free running period. The therapeutic value of circadian desynchronization noted by Stroebel may also be explainable by this model.

Breakdown of the P System: The P process, involving as it does a very complex form of feedback and optimization, is at least as prone to breakdown as any other control process, be it homeostasis in biology or feedback control engineering. In the former, the breakdown can result in fever, and so on, and in the latter it shows up in forms ranging from oscillations to total self-destruction. Both the control engineers and physicians spend most of their time correcting for instability and in attempting to avoid breakdown.

The analogy between fever and schizophrenia was noted by S. Cobb, who pointed out that there are at least seven different classes of conditions, which generally precede the schizophrenic reaction. He therefore regarded it as a common form of breakdown, like fever, and suggested that we do not need to regard it as a disease entity. In our model we regard schizophrenia as well as many other types of psychoses as forms of breakdown of the P system. For example, Freud's analogy between dream state thought content and the thought disturbances of an awake psychotic might be explained by saying that the brain is "stuck in the P mode of operation". This would also explain the lack of REM rebound in the schizophrenic as well as the lack of affect. Also the high percent of REM sleep observed in states of transition to psychosis would represent the unsuccessful "last stand" of the P system before it flipped into an abnormal form of stable but more or less nonfunctional operation.

CONCLUSION

Various forms of programming assumed to take place in the brain have been discussed. P or programming ability to cope was related specifically to REM sleep, and the consequences of this hypothesis regarding experimental tests and predictions were investigated. The large number of experimental questions raised by this model suggests that it may serve as a useful function in sleep research.

While the invention has been described in its presently preferred embodiment, it is understood that the words which have been used are words of description rather than words of limitation and that changes within the purview of the appended claims may be made without departing from the scope and spirit of the invention in its broader aspects.

What is claimed is:

1. A process of reducing vulnerability to brain damage by increasing REM sleep, said process comprising the steps of:

increasing amounts of REM sleep-enhancing activities, wherein said increasing step comprises maintaining a regular sleep schedule with a systematic schedule of phase changes in circadian rhythms to increase amounts of REM sleep; and diminishing REM sleep-reducers, wherein said diminishing step comprises reducing REM sleep-reducing drugs.

2. The process of reducing vulnerability to brain damage by increasing REM sleep as recited in claim 1, wherein the REM sleeping reducing drugs are selected from a group consisting of caffeine and tranquilizers.

* * * * *